United States Patent
Renaud

(10) Patent No.: US 12,251,258 B2
(45) Date of Patent: Mar. 18, 2025

(54) METHOD FOR CHARACTERISING AN OBJECT BY MEANS OF ULTRASONIC WAVES HAVING DIFFERENT MODES, USING A COMPOSITE IMAGE

(71) Applicants: SORBONNE UNIVERSITE, Paris (FR); CENTRE NATIONAL DE LA RECHERCHE SCIENTIFIQUE (CNRS), Paris (FR); INSERM (Institut National de la Santé et de la Recherche Médicale), Paris (FR)

(72) Inventor: Guillaume Renaud, Fontenay Aux Roses (FR)

(73) Assignees: SORBONNE UNIVERSITE, Paris (FR); CENTRE NATIONAL DE LA RECHERCE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 232 days.

(21) Appl. No.: 17/997,153

(22) PCT Filed: Apr. 26, 2021

(86) PCT No.: PCT/FR2021/050717
§ 371 (c)(1),
(2) Date: Oct. 26, 2022

(87) PCT Pub. No.: WO2021/219951
PCT Pub. Date: Nov. 4, 2021

(65) Prior Publication Data
US 2023/0087997 A1 Mar. 23, 2023

(30) Foreign Application Priority Data
Apr. 27, 2020 (FR) ...................................... 2004180

(51) Int. Cl.
*A61B 8/12* (2006.01)
*A61B 8/00* (2006.01)
*A61B 8/08* (2006.01)

(52) U.S. Cl.
CPC ............ *A61B 8/0875* (2013.01); *A61B 8/485* (2013.01); *A61B 8/5223* (2013.01)

(58) Field of Classification Search
CPC ...... A61B 8/0875; A61B 8/485; A61B 8/5223
See application file for complete search history.

(56) References Cited

U.S. PATENT DOCUMENTS

2004/0210135 A1   10/2004   Hynynen et al.

FOREIGN PATENT DOCUMENTS

WO   2019/016339 A1   1/2019

OTHER PUBLICATIONS

International Preliminary Report on Patentability received for PCT Patent Application No. PCT/FR2021/050717, mailed on Nov. 10, 2022, 16 pages (7 pages of English Translation and 9 pages of Original Document).

(Continued)

*Primary Examiner* — Mark D Remaly
(74) *Attorney, Agent, or Firm* — Thomas | Horstemeyer, LLP

(57) ABSTRACT

Disclosed is a method for characterising an object, comprising: emission of ultrasonic waves that enter an object by passing through an external interface, then reflect off an internal interface, then exit the object by passing through the external interface again, the ultrasonic waves comprising first waves having a mode that varies according to a first variation during their propagation in the object, and second waves having a mode that varies according to a second variation during their propagation in the object; reception of echo signals comprising first signals representing echoes of the first waves, and second signals representing echoes of the second waves, construction of a plurality of images showing the object, the plurality of images being constructed from the echo signals, under the assumption that two characteristics of the object are equal to two candidate values, and comprising a first image constructed from the first signals, and a second constructed from the second signals; construction of a composite image from the plurality of images; calculation of a focus metric in the composite (Continued)

image and, depending on the metric, selection or not of the two candidate values as values of the two characteristics. These characteristics can be used, in particular, to estimate a thickness of the object between the two interfaces.

21 Claims, 7 Drawing Sheets

(56) References Cited

OTHER PUBLICATIONS

International Search Report and Written Opinion received for PCT Patent Application No. PCT/FR2021/050717, mailed on Sep. 8, 2021, 20 pages (8 pages of English Translation and 12 pages of Original Document).

Napolitano et al., "Sound speed correction in ultrasound imaging", Ultrasonics, vol. 44, 2005, 16 pages.

Preliminary Research Report received for French Application No. 2004180, mailed on Feb. 4, 2021, 6 pages (1 page of French Translation Cover Sheet and 5 pages of original document).

Renaud et al., "In vivo ultrasound imaging of the bone cortex", Physics in Medicine and Biology, vol. 63, No. 12, Jun. 2, 2018, 17 pages.

Tang et al., "A Model-Based Approach to Investigate the Effect of a Long Bone Fracture on Ultrasound Strain Elastography", IEEE Transactions on Medical Imaging, vol. 37, No. 12, Dec. 2, 2018, 15 pages.

Treeby et al., "Automatic sound speed selection in photoacoustic image reconstruction using an autofocus approach", Journal of Biomedical Optics, vol. 16, No. 9, Sep. 2011, pp. 090501-1-090501-3.

METHOD FOR CHARACTERISING AN OBJECT BY MEANS OF ULTRASONIC WAVES HAVING DIFFERENT MODES, USING A COMPOSITE IMAGE

TECHNICAL FIELD

The present disclosure concerns a method for characterising an object by means of ultrasonic waves and a system for implementing this method.

This method and this system can advantageously be applied to characterise a bone.

STATE OF THE ART

The use of waves to characterise an object such as a living body, is known.

X-ray tomography imaging is, for example, a medical imaging technique using x-rays crossing through the body to be imaged. This technique can sometimes have the disadvantage of exposing the body to potentially-dangerous ionising radiation. Still today, we avoid exposing the bodies of young children to x-rays unless absolutely necessary.

Other known techniques aiming to characterise a living body use ultrasonic waves, which are less dangerous waves than x-rays.

Ultrasonic waves are conventionally transmitted by a array of transceivers, and their echoes on a body to be characterised are received by the same array or another array of transceivers after a certain propagation time between transmission and reception.

Images showing a section of the body in which the ultrasonic waves are propagated can then be constructed on the basis of echo signals received the by transceiver network (s).

When such images are constructed, the assumption is made that the body is a homogenous medium and that, consequently, the speed of sound is uniform in the body studied.

The speed of sound chosen is generally an average speed of sound in a non-bony biological tissue (skin or muscle, for example), which is generally around 1540 meters per second at an error close to 5 to 10%. The images obtained on the basis of this hypothesis thus have a satisfactory quality in the regions of interest showing a non-bony biological tissue.

However, the speed of sound in a bone (generally comprised between 2800 metres per second and 4200 metres per second for a compression wave in the cortical bone) is much higher than the speed of sound in a non-bone biological tissue. Images obtained on the basis of an assumption of uniform speed whose value corresponds to a speed of sound in a non-bone biological tissue have a poor quality in regions of interest showing bone. This poor quality is typically reflected by a low intensity and a blurry rendition of bone. For this reason, a common misconception in the medical community is that ultrasonic waves do not "easily penetrate" into bone.

The difference between the speed of sound in a bone and in the non-bone biological tissue surrounding the bone creates a refraction effect. It is therefore not possible to reconstruct good-quality images based on a predetermined value of the speed of sound in the bone, as we have already been able to do with a speed of sound in a non-bone biological tissue.

The speed of sound in a bone depends on several factors.

Firstly, the speed of sound in a bone varies from one individual to another. This is also the reason it constitutes very useful information to eventually diagnose problems such as osteoporosis.

Secondly, the speed of sound in a bone is not the same in all directions. In fact, bone is an elastically-anisotropic medium. This is especially due to the fact that so-called cortical bone comprises canals extending parallelly to the longitudinal axis of a long bone (tibia, for example), to house blood vessels, in particular. Thus, an ultrasonic compression wave propagates in a bone along a direction parallel to the longitudinal axis of a long bone more quickly than along another direction.

Ultimately, precisely determining the speed of sound is a major challenge to characterise a bone.

In this regard, a process has already been proposed for determining the speed of sound in a long bone parallelly to the longitudinal axis of the bone. During this process, ultrasonic waves are transmitted by an array of transceivers aligned parallelly to the longitudinal axis of a long bone. On the basis of the echo signals received by the receivers, a speed of a wave guided by the bone, called head wave, is determined, propagating along the outer surface of the bone. This speed is fairly easily determined by assuming that the relationship between the time of receiving an ultrasonic wave by one of the receivers and the distance separating this receiver from the transmitter of the same wave is a linear function.

However, this method cannot be used to determine a speed of sound in the bone along a direction other than a direction parallel to the longitudinal axis of a long bone. Consequently, it only permits partially characterising a bone.

Subsequently, document WO 2019/016339 proposed a method making it possible to overcome the problems above.

SUMMARY OF THE INVENTION

One objective of the present invention is to characterise more finely an object, such as a bone, for example.

To this end, according to a first aspect, a method for characterising an object is proposed comprising an external interface, an internal interface and an internal medium located between the external interface and the internal interface, the method comprising the steps of:
  transmission, by transmitters, of ultrasonic waves toward the object, so that ultrasonic waves propagate in an external medium located between the transmitters and the object, then enter into the object by crossing the external interface, then reflect on the internal surface, then exit the object by crossing the external interface again, the ultrasonic waves comprising first waves having a mode which evolves according to a first evolution during their propagation in the object and second waves having a mode which evolves according to a second evolution during their propagation in the object, the second evolution being different from the first evolution,
  reception, by receivers, of ultrasonic wave echo signals after they exit the object, the echo signals comprising first signals representing echoes of the first waves and second signals representing echoes of the second waves,
  determination of two characteristics of the object indicative of the propagation of ultrasonic waves in the object, the determination of two characteristics of the object comprising the following substeps:

a) construction of a plurality of images showing the internal interface and the internal medium, the plurality of images being constructed from the echo signals, location data of the external interface, a speed of sound in the external medium and under the assumption that the two characteristics of the object are respectively equal to two candidate values, the plurality of images comprising a first image associated with the first waves and constructed from the first signals and a second image associated with the second waves and constructed from the second signals, b) construction of a composite image from the plurality of images, c) calculation of a metric indicative of a focus quality of the internal interface and/or of the internal medium in the composite image, d) depending on the metric, selection or not of the two candidate values as respective values of the two characteristics of the object.

The method according to the first aspect can comprise the following optional characteristics, taken alone or combined together whenever this is technically possible.

Preferably:

the ultrasonic waves comprise third waves having a mode which evolves according to a third evolution during their propagation in the object, the third evolution being different from the first evolution and the second evolution, the echo signals comprise third signals representing echoes of the third waves, the plurality of images comprises a third image associated with the third waves and constructed from the third signals.

Preferably:

the ultrasonic waves comprise fourth waves having a mode which evolves according to a fourth evolution during their propagation in the object, the fourth evolution being different from the first evolution, the second evolution and the third evolution, the echo signals comprise fourth signals representing echoes of the fourth waves, the plurality of images comprises a fourth image associated with the fourth waves and constructed from the fourth signals.

Preferably, the Ultrasonic Waves Comprise:

waves having a mode which does not change when crossing the external interface and does not change when reflecting on the internal interface and/or waves having a mode which changes when they enter into the object by crossing the external interface, which does not change when they are reflected on the internal interface and which changes again when they exit the object by crossing the external interface and/or waves having a mode which changes when they enter into the object by crossing the external interface, which changes again when they are reflected on the internal interface and which does not change when they exit the object by crossing the external interface and/or waves having a mode which does not change when they enter into the object by crossing the external interface, which changes when they are reflected on the internal interface and which changes again when they exit the object by crossing the external interface.

Preferably, the ultrasonic waves are compression waves at their emission.

In one embodiment, the two characteristics of the object comprise an elastic anisotropy parameter of the object and a propagation speed of vertically polarised shear waves in the object in a direction of propagation parallel or perpendicular to a longitudinal axis of the object.

In another embodiment, the two characteristics of the object comprise a propagation speed of compression waves in the object and a propagation speed of shear waves in the object.

The two parameters can be adapted to define, in combination with two other parameters:

a calculation function of a propagation speed of a compression wave in the object in any direction of propagation and a calculation function of a propagation speed of a shear wave in the object with vertical polarisation and in any direction of propagation.

The two other parameters can comprise a propagation speed of compression waves in an axial direction of the object and another parameter of elastic anisotropy of the object.

The plurality of images can be constructed under the assumption that the object is elastically isotropic in a plane perpendicular to a longitudinal axis of the object or under the assumption that the object is elastically isotropic.

Preferably, the construction of a reference image comprised in the plurality of images, and associated with reference waves, comprises:

an estimate of the trajectories followed by the reference waves, from reference signals representing the echoes of the reference waves, location data of the external interface and under the assumption that the two characteristics of the object are respectively equal to two candidate values, a calculation of the duration of propagation of ultrasonic waves via the estimated trajectories, calculation of an intensity of a pixel of the reference image, from propagation times, reference signals and positions of transmitters and receivers.

Preferably, the construction of the composite image comprises a weighted sum of the plurality of images.

Preferably, the method according to the first aspect comprises a repetition of substeps a) to c) for different pairs of candidate values, so as to obtain a plurality of metrics, one of the pairs of candidate values being selected at step d) according to the plurality of metrics.

Preferably, the method comprises a location of the internal interface in an image constructed during an implementation of step a) or of step b), so as to generate location data of the internal interface.

Preferably, the internal interface is located in an image constructed from two candidate values selected at step d) as the respective values of the two characteristics of the object.

Preferably, the internal interface is located in an image constructed from wave echo signals having a mode which does not change when crossing the external interface and which does not change when reflecting on the internal interface.

Preferably, the method comprises an estimate of a thickness of the object between the external interface and the internal interface, from location data of the external interface and location data of the internal interface.

In a particular application of the method, the object is a bone. Preferably, the external interface is a bone periosteum.

Preferably, the internal interface is a bone endosteum. Preferably, the internal interface is a bone cortical tissue.

The internal medium can comprise pores containing a fluid or solid fibres oriented in the same longitudinal direction. A system is also proposed for characterising an object, the system comprising:
- transmitters configured to transmit ultrasonic waves toward the object, so that ultrasonic waves propagate in an external medium located between the transmitters and the object, then enter into the object by crossing the external interface, then reflect on the internal surface, then exit the object by crossing the external interface again, the ultrasonic waves comprising first waves having a mode which evolves according to a first evolution during their propagation in the object and second waves having a mode which evolves according to a second evolution during their propagation in the object, the second evolution being different from the first evolution,
- receivers configured to receive ultrasonic wave echo signals after they exit the object, the echo signals comprising first signals representing echoes of the first waves and second signals representing echoes of the second waves,
- a processing device configured to determine two characteristics of the object indicative of the propagation of ultrasonic waves in the object, the determination of two characteristics of the object comprising the following substeps:
  a) construction of a plurality of images showing the internal interface and the internal medium, the plurality of images being constructed from the echo signals, location data of the external interface, a speed of sound in the external medium and under the assumption that the two characteristics of the object are respectively equal to two candidate values, the plurality of images comprising a first image associated with the first waves and constructed from the first signals, and a second image associated with the second waves and constructed from the second signals,
  b) construction of a composite image from the plurality of images,
  c) calculation of a metric indicative of a focus quality of the internal interface and/or of the internal medium in the composite image,
  d) depending on the metric, selection or not of the two candidate values as respective values of the two characteristics of the object.

DESCRIPTION OF THE FIGURES

Other characteristics, objectives and advantages of the invention will appear from the following description, which is purely illustrative and non-limiting and should be read with regard to the attached drawings, in which.

Throughout the figures, similar elements bear identical references.

DETAILED DESCRIPTION OF EMBODIMENTS

1) Characterisation System

Figure 1:
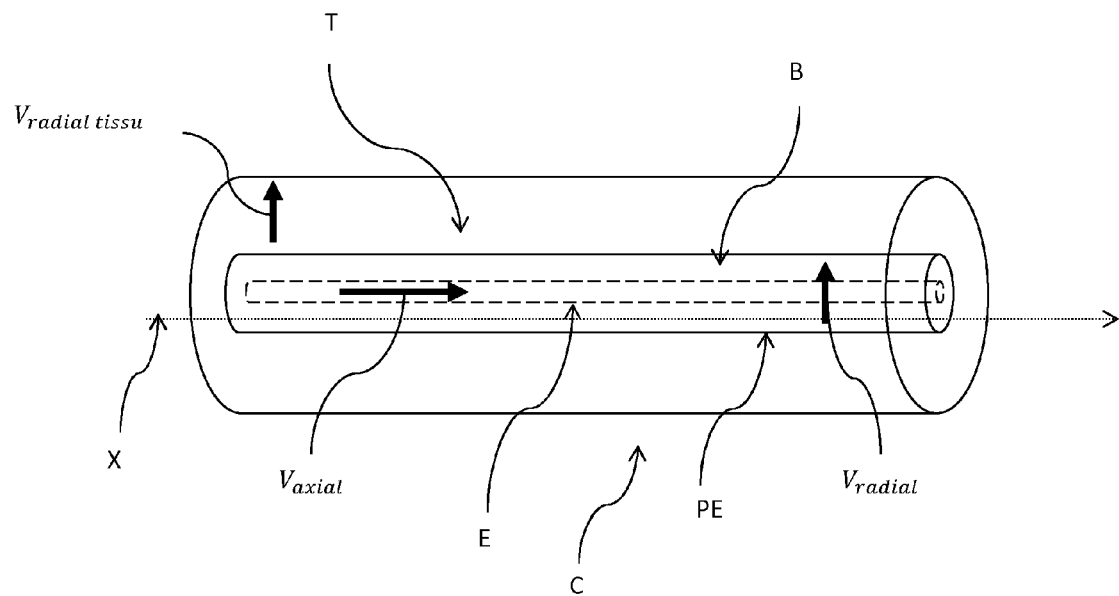
FIG. 1 is a schematic view of a body comprising a bone.

FIG. 1 schematically illustrates an example of a part of a body C comprising a bone B and non-bone biological tissue T.

The bone B extends along a longitudinal X axis. Bone B especially comprises marrow, an endosteum E extending around the marrow, a cortical bone tissue T extending around the endosteum E and a periosteum extending around the cortical bone tissue T.

The cortical tissue comprises osteons or Haversian canals, each osteon defining a pore having a cylindrical shape oriented parallelly to the longitudinal X axis.

The non-bone biological tissue T extends around the bone and more specifically around the periosteum PE with which it is in contact. The non-bone biological tissue T comprises flesh and possibly a skin surrounding the flesh.

The periosteum PE is an external interface of the bone B, between an external medium (the non-bone biological tissue T) and in internal medium (the cortical bone tissue).

The endosteum E is also an internal interface of bone B between the cortical bone tissue T and the marrow.

Figure 2:
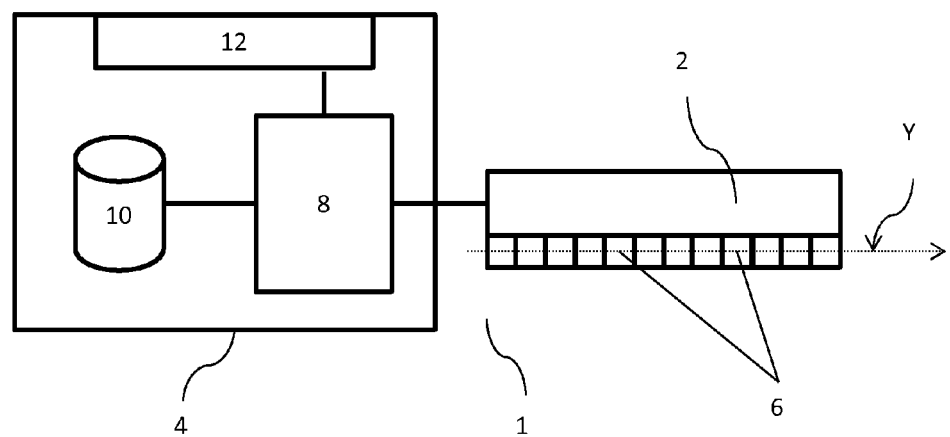
FIG. 2 illustrates a characterisation system according to one embodiment.

In reference to FIG. 2, a characterisation system 1 comprises an ultrasound probe 2, a device 4 for processing echo signals acquired by the probe 2 and optionally a display screen 12.

The ultrasound probe 2, known in and of itself, comprises at least one array of transceivers 6 aligned along a Y axis.

Conventionally, probe 2 comprises a silicone lens (not illustrated) arranged in front of the row of transceivers 6.

Each transceiver 6 is suited to transmit ultrasonic waves.

Each transceiver 6 is also suited to acquire ultrasonic wave echo signals transmitted by any other transceiver 6.

A transceiver is, for example, a piezoelectric element.

The relative positions of transceivers 6 are predetermined. Typically, transceivers 6 are separated by a constant pitch along the axis of the probe 2.

Furthermore, the echo signal processing device 4 conventionally comprises at least one processor 8 and one memory 10.

The processor 8 is configured to execute calculations and, in particular, an image processing algorithm whose operation will be detailed below.

One function of the processing device 4 is to determine, from echo signals and other data, at least two parameters of the bone indicative of the propagation of ultrasonic waves in the bone.

The memory 10 stores predetermined data. These data are not specific to an individual's body but rather are generic data applicable to any individual of a population.

The predetermined data comprise a collection of candidate values for two bone parameters indicative of the propagation of ultrasonic waves in the bone.

2) First Embodiment of a Characterisation Method, Based on a Transverse Elastic Isotropy Model A method for characterising the bone B by means of the characterisation system 1 and according to a first embodiment comprises the following steps.

Figure 3:
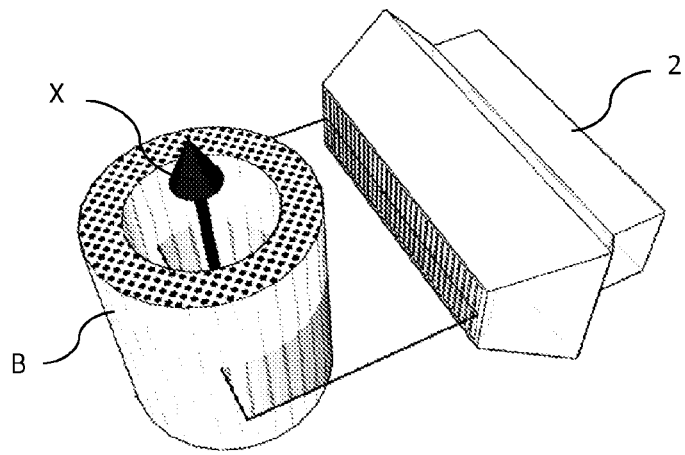
FIG. 3 represents a bone and a wave in a first position.

The probe 2 is positioned near the body C in a first position illustrated in FIG. 3. In the first position, the transceivers 6 of the probe 2 are aligned essentially perpendicularly to the longitudinal axis of the bone B. In other words, the Y axis of probe 2 is perpendicular to the X axis of the bone B in the first position.

Figure 4:
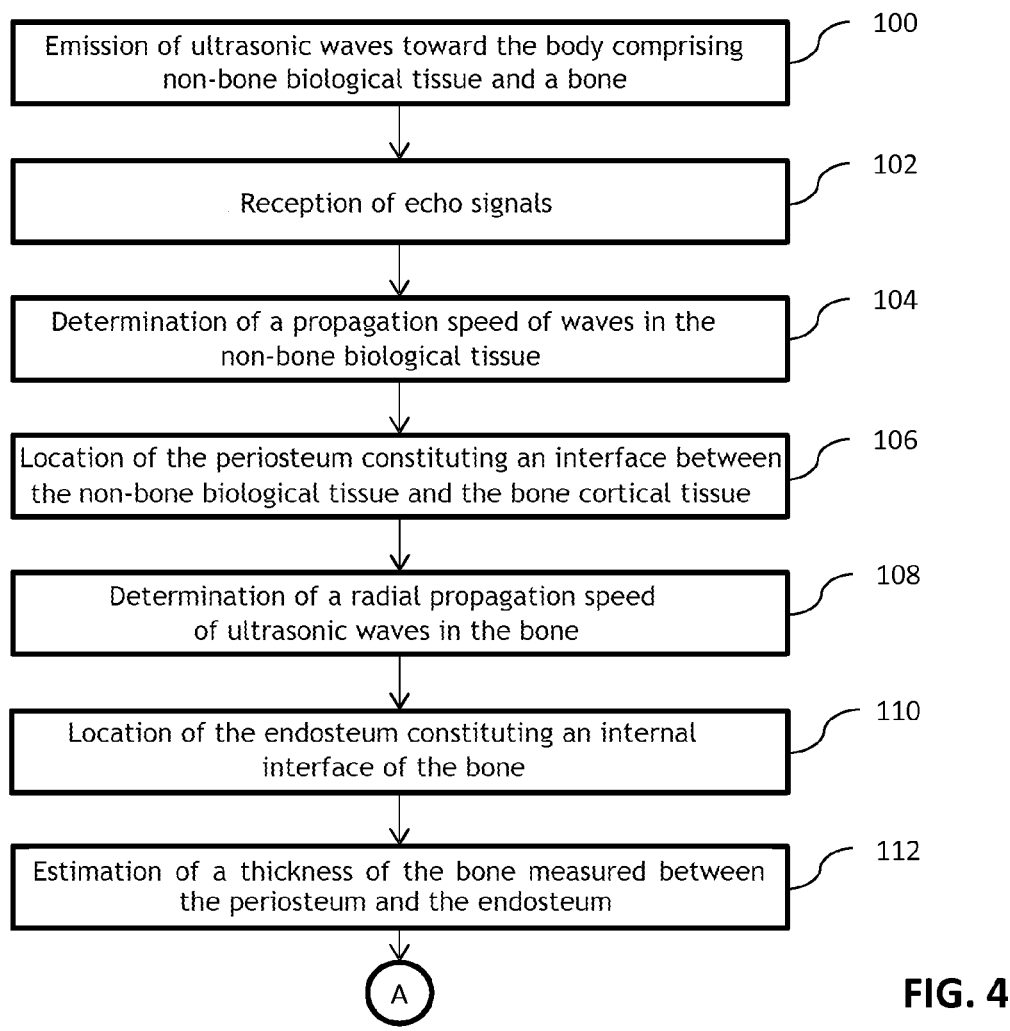
FIG. 4 is a flow chart of the steps of a characterisation method according to a first embodiment.

In reference to FIG. 4, the probe 2 transmits ultrasonic waves in the direction of the body C (step 100). These waves are, for example, radial compression waves. These waves propagate in a plane perpendicular to the longitudinal X axis of bone B, also known as the transverse plane. The ultrasonic waves propagate in the non-bone biological tissue (external medium located between the transmitters and the bone), then enter the bone by crossing the periosteum (external interface of the bone), then reflect on the endosteum (internal interface of the bone), then exit the bone by crossing the periosteum again.

The ultrasonic waves transmitted during this step 100 can have a compression mode (the wave is therefore a compression wave) or a shear mode (the wave is therefore a shear wave).

The echo signals of these ultrasonic waves are acquired by the transceivers of probe 2 (step 102). Of course, a wave transmitted by a transceiver 6 of index i can perfectly give rise to an echo signal received by another transceiver 6 of index j.

The echo signals are digitized, transmitted to the processing device 4 and stored in the memory 10 in a form known from the state of the art.

Next, the processor 8 implements the following steps, which are described in document WO 2019/016339:

Determining a speed of sound in the biological tissue (step 104). This step uses the echo signals received in step 102. The speed of sound in the biological tissue determined in step 102 is a radial speed $V_{radial\ tissu}$, that is to say in a transverse plane (perpendicular to the longitudinal X axis of the bone).

Locating the periosteum PE (step 106). As previously indicated, the periosteum PE is an external interface of the bone B between an internal medium of the bone B (i.e., the cortical tissue) and an external medium (i.e., the non-bone biological tissue T surrounding the bone B). In other words, the periosteum defines a demarcation curve. During the location step 106, the processor 8 generates location data of the periosteum PE.

Determining a radial speed of sound in the bone $V_{radial}$ (step 108). This speed is therefore a speed in a plane perpendicular to the longitudinal axis of the bone. The speed $V_{radial}$ is determined from location data of the periosteum PE obtained in step 106 and the speed $V_{radial\ tissu}$ determined in step 104.

As a reminder, step 108 comprises the following substeps:

Construction of an image, called preliminary image, showing the cortical bone tissue of bone B and the endosteum E, from echo signals, of the speed $V_{tissu}$, location data of the periosteum PE and under the assumption that the speed $V_{radial}$ is equal to a candidate value stored in the memory. The preliminary image is, for example, constructed by means of the Kirchhoff migration method called "total focusing method" or even the so-called "reverse time migration" method (RTM).

Calculation of a metric, called preliminary metric, representing a focus quality in a region of interest of the preliminary image. The region of interest chosen is typically a region showing the endosteum E and/or the cortical bone tissue B.

Repetition of the preceding two substeps for different candidate values available in the memory so as to obtain several preliminary metrics, Selection as a definitive value for the speed $V_{radial}$ of an optimal value among the candidate values used. The processor 8 is based on the preliminary metrics for this.

The processor 8 locates the endosteum E (step 110) in one of the preliminary images constructed during step 108. During the location step 110, the processor 8 generates location data of the endosteum E.

The step 110 of locating the endosteum E conventionally comprises the following substeps:

The preliminary image chosen for the location is subjected to a segmentation, so as to identify a group of pixels (this segmentation comprising, for example, the implementation of Dijkstra's algorithm known from the state of the art).

This group of pixels is approximated into a demarcation curve defined by a polynomial, for example a parabola.

Preferentially, the locating step 110 is implemented in the preliminary images constructed on the basis of candidate values having been selected as such $V_{radial}$ in step 109. This has the advantage of locating the endosteum E more precisely due to the high focus quality of this image among all those which have been constructed by the processor 8 during the step 108.

Next, the processor 8 estimates a thickness of the bone B, measured between the periosteum PE and the endosteum E (step 112). This thickness is estimated on the basis of location data obtained in steps 106 and 110.

Figure 5:
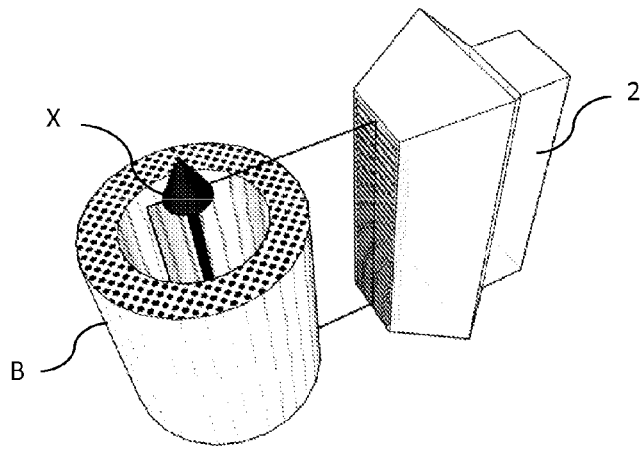
FIG. 5 represents a bone and a wave in a second position.

Next, the probe 2 is positioned near the body C in a second position illustrated in FIG. 5. The second position is different from the first position. Indeed, in the second position, the X and Y axes are coplanar, even parallel.

Figure 6:
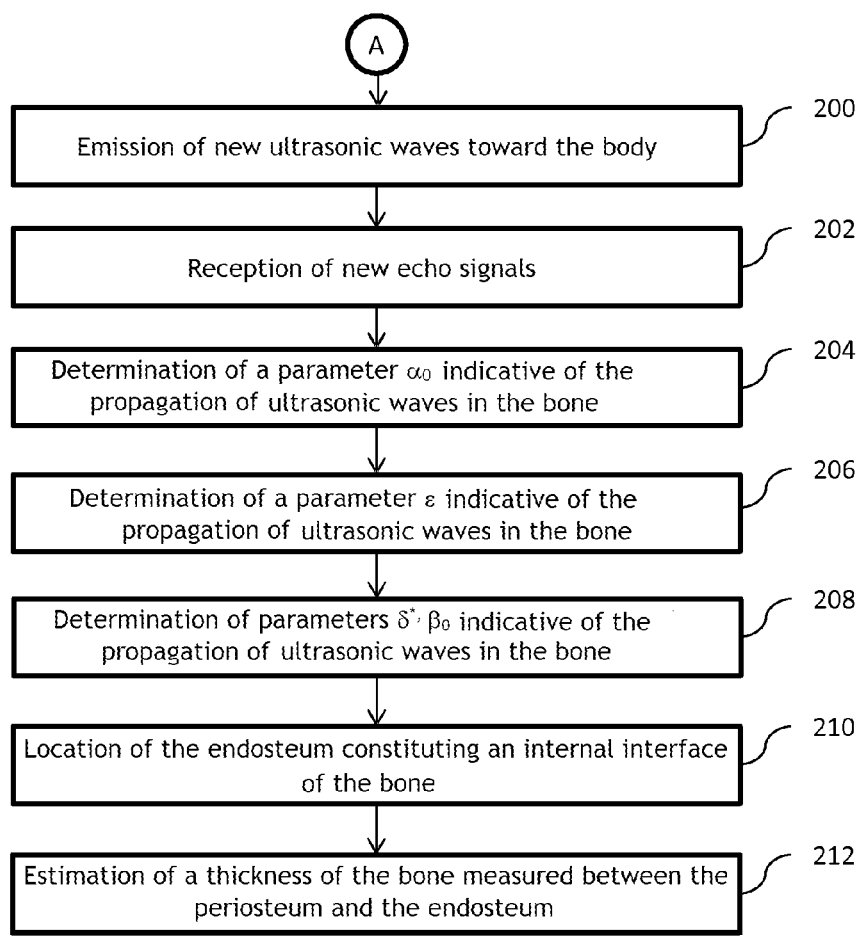
FIG. 6 is a flow chart of the steps of a characterisation method according to the first embodiment.

In reference to FIG. 6, the probe 2 in the second position transmits new ultrasonic waves in the direction of the bone B (step 200). The new ultrasonic waves propagate in a longitudinal plane parallel to the longitudinal axis of the bone B.

The new ultrasonic waves enter into the body C, then propagate in the non-bone biological tissue T (external medium), then enter into the bone B by crossing the periosteum PE (external interface of the bone), then propagate in the bone cortical tissue (internal medium). The new waves then reflect on the endosteum E (internal interface), then propagate again in the bone cortical tissue, then exit the bone by crossing the periosteum PE again, propagate again in the non-bone biological tissue T before leaving body C to reach the receivers of the probe 2.

A new ultrasonic wave can have a compression mode (the wave is therefore a compression wave) or a shear mode (the wave is therefore a shear wave).

Moreover, the mode of a new ultrasonic wave is able to evolve between its transmission by a transmitter of the probe 2 and its subsequent reception by a receiver of the probe 2. Two mode changes are likely to occur: compression mode to shear mode or shear mode to compression mode.

The ultrasonic waves have a compression mode when transmitted by the probe 2 in step 200.

However, the new ultrasonic waves transmitted in step 200 comprise waves whose respective modes evolve differently during their propagation in the bone B. Moreover, the trajectories followed by these waves are also different.

The new ultrasonic waves can comprise first waves whose mode evolves according to a first evolution during their propagation in the bone: their mode does not change when crossing the periosteum PE (external interface) and does not change when reflecting in the endosteum (internal interface). These first waves are, for example PPPP waves: before reaching the bone, these PPPP waves are compression waves and remain so during their propagation in the bone. The first waves follow first trajectories in the bone.

The new ultrasonic waves comprise second waves whose mode evolves according to a second evolution during their propagation in the bone, the second evolution being different from the first evolution: their mode changes when they enter into the bone B by crossing the periosteum PE (external interface), does not change when reflecting in the endosteum (internal interface) and changes again when they exit the object by crossing the periosteum (external interface). These second modes are, for example PSSP waves: before reaching the bone, these waves are compression waves, transform into shear waves when entering into the bone B by the periosteum PE and transform into compression waves when leaving the bone by crossing the periosteum PE again. The second waves follow second trajectories in the bone which are different from the first trajectories.

The new ultrasonic waves can comprise third waves whose mode evolves according to a third evolution during their propagation in the bone, the third evolution being different from the first evolution and the second evolution. These third waves have a mode which changes when they enter into the bone B by crossing the periosteum PE (external interface), which changes again when they are reflected in endosteum E (internal interface) and which does not change when they exit the bone by crossing the periosteum PE (external interface). These third waves are, for example, PSPP waves: before reaching the bone, these waves are compression waves, transform into shear waves when entering into the bone B by the periosteum PE and retransform into compression waves when reflecting in the endosteum E. The third waves follow third trajectories in the bone which are different from the first trajectories and the second trajectories.

The new ultrasonic waves can comprise fourth waves whose mode evolves according to a fourth evolution when they are propagated in the bone, the fourth evolution being different from the first evolution, the second evolution and the third evolution. These fourth waves have a mode which does not change when they enter into the bone by crossing the periosteum PE (external interface), which changes when they are reflected in the endosteum E (internal interface) and which changes again when they exit the bone by crossing the periosteum PE (external interface). These fourth waves are, for example, PPSP waves: before reaching the bone, these waves are compression waves, transform into shear waves when reflecting in the endosteum and retransform into compression waves when leaving the bone by crossing the periosteum. The fourth waves follow fourth trajectories in the bone which are different from the first trajectories, the second trajectories and the third trajectories.

Figure 7:
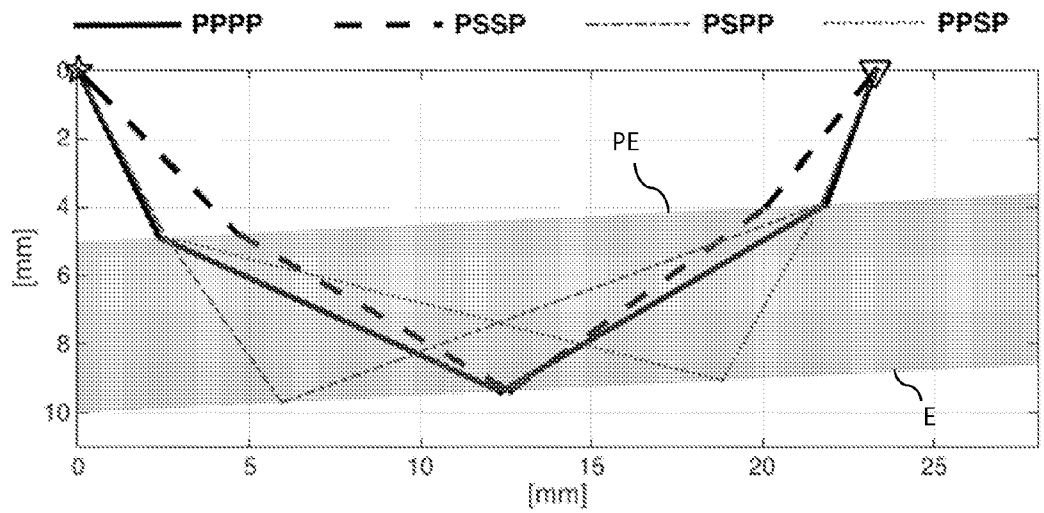
FIG. 7 illustrates the trajectories followed by different types of waves in a bone.

FIG. 7 shows the respective trajectories of a PPPP wave, a PSSP wave, a PSPP wave and a PPSP wave as well as a PP wave. FIG. 7 shows a gray zone which represents the cortical tissue of bone B. The periosteum PE is represented by the upper border of this gray zone and the endosteum E is represented by the lower border of this gray zone.

The new ultrasonic waves transmitted in step 200 comprise the first, second, third and fourth waves mentioned above. We will see in the following that these different types of waves are exploited to characterise the bone B more precisely.

The new echo signals of these new ultrasonic waves are acquired by the transceivers 6 of the probe 2 (step 202).

The new echo signals comprise different signals respectively associated with the different modes described previously, whose modes evolve differently and follow different trajectories when propagating in the bone.

Thus, the new echo signals obtained in step 202 can comprise:
first signals constituting echoes of the first waves and/or
second signals constituting echoes of the second waves and/or
third signals constituting echoes of the third waves and/or
fourth signals constituting echoes of the fourth waves.

It is well known to the skilled person that a compression wave is faster than a shear wave. For example, the propagation speed of a compression wave in a bone is between 2800 and 4200 metres per second, while the propagation speed of a shear wave in a bone is between 1300 and 2000 metres per second. In other words, a compression wave is about twice as fast in a bone than a shear wave. It is also well known to the skilled person that shear waves propagate in a soft tissue such as biological tissue T at a negligible speed of around 1 metre per second.

Due to this physical phenomenon which is verified not only for bone but also for any other propagation medium, the echoes of the first, second, third and fourth waves are received by a different receiver 6 at different times. The PPPP waves are received first by a receiver 6, then these waves are kept in a compression mode (fast) during their propagation in the bone B. The PSSP waves are received by the same receiver 6 at a later time and even last because these waves are propagated in the bone according to a shear mode both going out and coming back. The PSPP and PPSP waves are received by the same receiver after the PPPP waves and before the PSSP waves; indeed, these waves are slowed by their shear mode but only going out or coming back into the bone (either before reaching the endosteum or after having been reflected in the endosteum).

The new echo signals are digitized, transmitted to the processing device 4 and stored in the memory 10.

The processing implemented by the processing device 4 on the basis of these new echo signals will now be described.

These treatments are based on the assumption that the bone B is elastically isotropic in the transverse plane (which is perpendicular to the longitudinal X axis).

Under this assumption, it is possible to calculate the propagation speed $v_P(\theta)$ of a compression wave in a direction of propagation forming any angle $\theta$ with the transvers plane of the bone and the propagation speed $v_{SV}(\theta)$ of a shear wave with vertical polarisation in the same direction of propagation, by using two functions $v_P$ and $v_{SV}$.

These two functions $v_P$ and $v_{SV}$ can be defined by four parameters, called Thomsen parameters because they were proposed by L. Thomsen in the document entitled "Weak elastic anisotropy", published in 1986.

In fact, we have:

$$v_P(\theta) = \alpha_0 \left[ 1 + \epsilon\cos^2(\theta) + D^*(\theta, \alpha_0, \beta_0, \epsilon, \delta^*) \right]^{\frac{1}{2}}$$

-continued $$v_{SV}(\theta) = \beta_0\left[1 + \left(\frac{\alpha_0^2}{\beta_0^2}\right)(\epsilon\cos^2(\theta) - D^*(\theta, \alpha_0, \beta_0, \epsilon, \delta^*))\right]^{\frac{1}{2}}$$

where:

$$D^* = \frac{1}{2}\left(1 - \frac{\beta_0^2}{\alpha_0^2}\right)\left[\left(1 + \frac{4\delta^*}{\left(1 - \frac{\beta_0^2}{\alpha_0^2}\right)^2}\cos^2(\theta)\sin^2(\theta) + \frac{4\left(1 - \frac{\beta_0^2}{\alpha_0^2} + \epsilon\right)\epsilon}{\left(1 - \frac{\beta_0^2}{\alpha_0^2}\right)^2}\cos^4(\theta)\right)^{\frac{1}{2}} - 1\right]$$

The Thomsen parameters comprise:

$\alpha_0$: axial propagation speed of a compression wave in the bone B, i.e., in a direction parallel to the longitudinal X axis of the bone B. We also note this speed $V_{axial}$.

$\beta_0$: propagation speed of a shear wave in the bone B for $\theta=0$ (radial direction, which can also be called transverse direction) or $\theta=\pi/2$ (axial direction). These two values are also considered in this model.

$\delta^*$: elastic anisotropy parameter in the bone B.

$\epsilon$: other elastic anisotropy parameter in the bone B. As we will see below, this other elastic anisotropy parameter is representative of a gap between the axial propagation speed in bone of a compression wave and a radial speed in bone of a compression wave.

The processor 8 determines the parameter $\alpha_0$ on the basis of new echo signals (step 204). This step can be based, for example, on an identification of a head wave which propagates along the outer surface of the bone B. According to this known technique, two specific echo signals are used, acquired in response to the transmission of waves by two extremal transmitters 6 of the probe 2 (typically, that of index 0 and that of maximum index). All the transceivers 6 receive the waves selectively transmitted by one of the extremal transceivers 6 of the probe 2. The distance which separates the two transmitters 6 is known, typically between 10 and 40 millimeters. At this scale, it can be assumed that the outer surface of the bone B is flat. As a result, the propagation speed of a head wave along this surface can be easily determined given that the relationship between time of arrival of the head wave of a wave by one of the two transceivers 6 used and the distance separating one of the two extremal transmitters 6 and the receivers 6 is a linear function. Under this assumption of linearity, it is very easy to determine:

The speed V1 of a head wave which is propagated along the bone B when the transceiver 6 of index 0 was used as a transmitter and all the transceivers 6 were used as receivers.

The speed V2 of a head wave which is propagated along the bone B when the transceiver 6 of maximal index was used as a transmitter and all the transceivers 6 were used as receivers.

The parameter $\alpha_0$ is then calculated by the processor 8 by means of the following formula:

$$\alpha_0 = V_{axial} = \frac{2V_1 V_2 \cos(\alpha)}{V_1 + V_2}$$

The processor 8 also determines the parameter E (step 206) on the basis of the speed $V_{radial}$ obtained in step 108 and the speed $V_{axial}$ (also called the parameter $\alpha_0$) obtained in step 204.

The processor 8 typically carries out the following calculation during step 206 to determine the parameter $\epsilon$:

$$\epsilon = \frac{(V_{radial})^2 - (V_{axial})^2}{2(V_{radial})^2}$$

Figure 8:
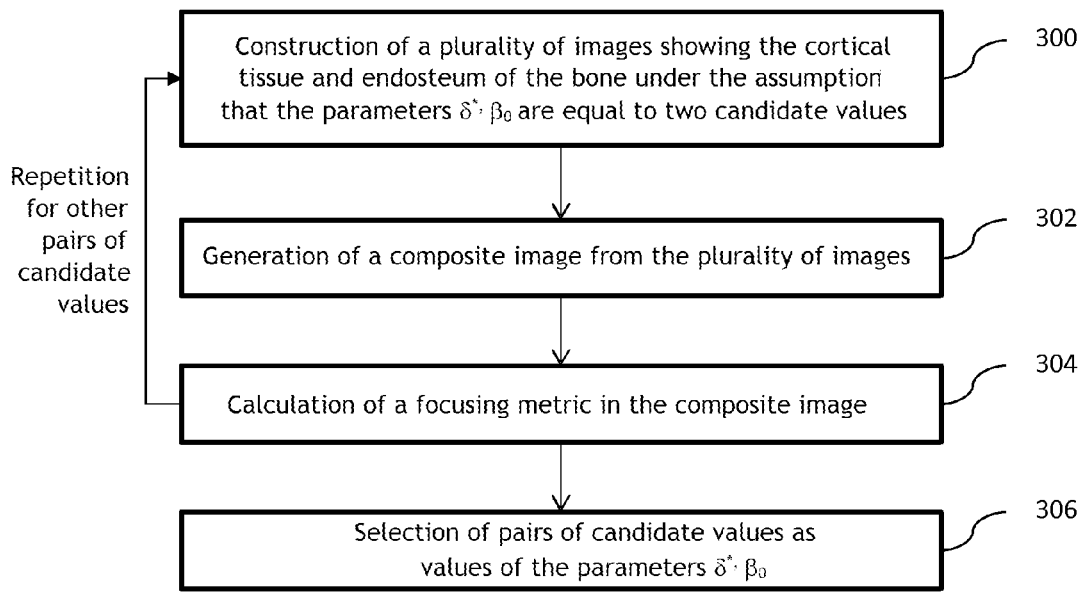
FIG. 8 is a flow chart detailing the substeps of a step illustrated in FIG. 6.

The processor 8 also determines parameters $\delta^*$ and $\beta_0$ using the new echo signals (step 208). In reference to FIG. 8, this step 208 comprises the following substeps.

The processor 8 constructs a plurality of images each showing the endosteum E (internal interface) and the cortical tissue of the bone (internal medium) (step 300). For this construction, the following input data are used by the processor 8:

The new echo signals obtained in step 202.

The location data of the periosteum PE (external interface) obtained in step 106.

The speed of sound in the biological tissue T (external medium) determined in step 108.

Two candidate values which are available in the memory 10.

To construct the plurality of images in step 300, the processor 8 implements a processing making the assumption that the parameters $\delta^*$ and $\beta_0$ are respectively equal to these two candidate values.

Each image of the plurality of images is made up of a pixel grid, each pixel being defined by a position in the grid and by an intensity I, this intensity being typically representative of a grey level. Each preliminary image also represents a sectional view of a body C in a plane in which ultrasonic waves are propagated (this sectional plane is parallel to the axis of probe 2). Each point of this sectional plane will thus be shown in a pixel of each image.

In return, the echo signals acquired in step 202 are not used to construct an image of the plurality of images. Only one of the four types of echo signals mentioned above is used to construct an image of the plurality of images. Consequently, an image of the plurality of images is associated with waves having a specific mode evolution and having followed a specific trajectory during their propagation in the bone.

In reference to FIGS. 9a to 9d, the plurality of images can thus comprise:

a first image I1 selectively constructed on the basis of the first echo signals, when the first waves are part of the ultrasonic waves transmitted in step 202 and/or a second image I2 selectively constructed on the basis of the second echo signals, when the second waves are part of the ultrasonic waves transmitted in step 202 and/or a third image I3 selectively constructed on the basis of the third echo signals, when the third waves are part of the ultrasonic waves transmitted in step 202 and/or a fourth image I4 selectively constructed on the basis of the fourth echo signals, when the fourth waves are part of the ultrasonic waves transmitted in step 202.

In a variant of embodiment, an image is constructed from the plurality of images by means of the Kirchoff migration method or the so-called "total point focusing method". These methods are known in and of themselves.

The construction of the first image I1 by means of one of the two methods comprises the following substeps.

For a given point P of the body C studied, the processor 8 selectively estimates the first trajectories followed by the first waves, from the first echo signals and under the assumption that the parameters δ* and β₀ are respectively equal to two candidate values present in the memory 10.

The first waves passed by the point P have been transmitted by a transmitter of index i, whose position is known along the Y axis of the probe 2 and received by a receiver of index j whose position is also known along the Y axis of the probe 2. There are therefore at most as many first wave echo signals passed through the point P as there are pairs (i, j) of transmitter/receiver indices in the probe 2 (therefore at most M×N signals if M is the number of transmitters used and N the number of receivers used).

The estimation of the first trajectories is implemented by exploiting the Fermat principle according to which it is supposed that a first wave propagates rectilinearly in a homogenous medium. The body C is considered during the implementation of this estimation of the first trajectories as a heterogeneous medium: the non-bone biological tissue is considered as a homogeneous tissue, in which the first ultrasonic waves are propagated at the speed $V_{radial\_tissu}$ determined previously.

Furthermore, the bone B is considered as another homogeneous medium in which these first waves are propagated at speeds calculated by means of the two Thomsen function described above, making the assumption that the parameters δ* and β₀ used by these functions are respectively equal to two candidate values and that the parameters α₀ and ∈ are equal to the values determined previously in steps 204 and 206.

It is also considered that the periosteum, whose location is known via the data obtained in step 104, induces a refraction of the first waves.

The processor 8 then calculates the durations of propagation of the first waves passed by the point P via the first trajectories estimated.

A duration of propagation is broken down into a duration of propagation $t_T(i,P)$ from the transmitter of index i up to the point P and a duration of propagation $t_R(j,P)$ from the point P up to a receiver of index j.

The processor 8 then calculates an intensity of a pixel of the first image I1 at the point P considered, from the estimated propagation times, the first echo signals and the positions of the transmitters and receivers.

The intensity of the point P is typically calculated via the formula below:

$$I(P) = \sum_{i=1}^{M}\sum_{j=1}^{N} W(P, i, j) \times D(t = t_T(i, P) + t_R(j, P), i, j)$$

wherein:
- $D(t=t_T(i,P)+t_R(j, P), i, j))$ designates a data point representative of a first echo signal received at time t by the receiver of index j, the echo originating from a first wave initially transmitted by the transmitter of index i,
- W(P, i, j) designates a weight obtained by an application of a predetermined weighting function W.

Typically, the weighting function W is an observation window function (also called weighting or apodization window in the literature). We have W(P,i,j)=1 if the angle of the segment of the return path of the first wave going from the point P to the receiver of index j, relative to a direction normal to a transmission/reception plane of the probe 2, is less than a predetermined angular threshold, and we have W(P,i,j)=0 if not. This angular threshold is, for example, fixed at 50 degrees (this angle corresponding to a loss of sensitivity of a receiver of around 50%).

By repeating the substeps which precede at several points P, the first image I1 can be entirely constructed.

In another variant of embodiment, the first image I1 is constructed by means of the first so-called "reverse time migration" (RTM) method. This method is an alternative imaging method leading to an image representing the reflectivity of a region at any point thereof. It supposes knowledge of the geometry of the medium studied and the propagation speed of the first waves at each point. The reflectivity image is obtained by calculating, at any point of the image, a temporal correlation between an incident field generated by the source and the back-propagated field recorded by the receivers. These fields are obtained by numerically solving the acoustic (or elastic) wave equation, using, respectively, the waveform generated by a transmitter and the echo signals recorded by the receivers (reversed in time) as boundary conditions. These operations must be repeated for each transmission. The final image is obtained by summing the images obtained for each transmission. However, this method is much more costly in calculation time that the one used in the preferred variant of embodiment described previously.

Regardless of the variant of embodiment used, the first image I1 is constructed by selectively using the echo signals of the first waves, which are propagated by following the particular trajectories (the first trajectories), with a particular mode evaluation (no change of mode on crossing the periosteum PE and reflecting in the endosteum E). Thus, the second, third or fourth echo signals, if present, are not used to construct the first image I1.

The second image I2, the third image I3 and the fourth image I4 are constructed using one of the variants of embodiment described above, the single difference residing, of course, in the echo signals selectively used each time. Thus, only the second echo signals are used to construct the second image I2, only the third echo signals are used to construct the third image I3, and only the fourth echo signals are used to construct the fourth image I4.

As shown by FIGS. 9a to 9d, the images I1-I4 constructed during step 300 give different visual information on the cortical bone tissue and endosteum. This arises from the fact that these images have been constructed on the basis of waves having followed different trajectories and whose modes have evolved differently during their propagation in bone B.

Figure 9A:
FIGS. 9a to 9e respectively show five images constructed during the implementation of a characterisation method.
Figure 9B:
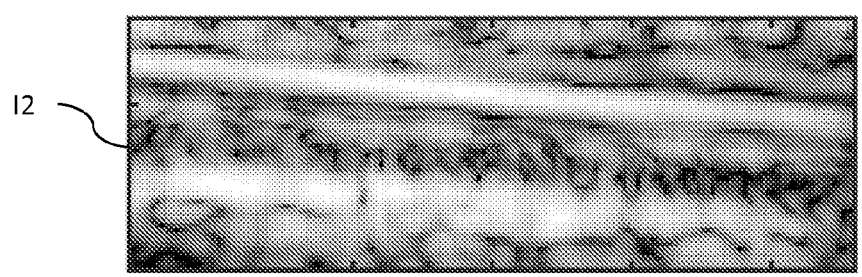
Figure 9C:
Figure 9D:
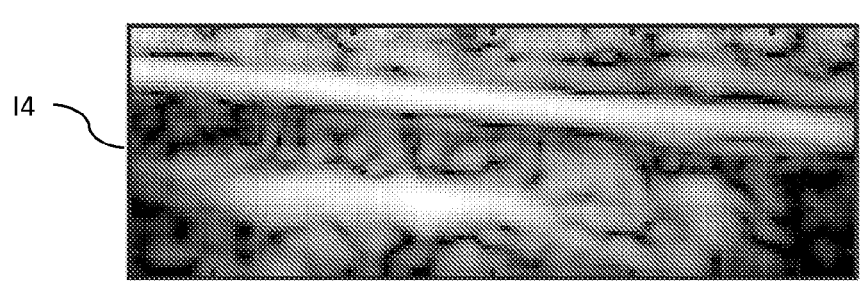
Figure 9E:
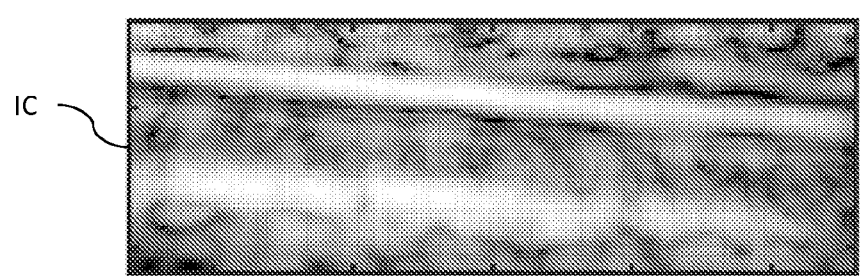

The processor 8 then generates a composite image IC from the plurality of images previously constructed (step 302). This composite image IC, an example of which is shown in FIG. 9e, thus combines the different visual information mentioned above, in a synergistic manner. Thus, the composite image IC gives more visual information on the bone than each image of the plurality of images taken individually.

This composite image IC can be a weighted sum of the plurality of images. It is, in particular, possible to implement an incoherent compounding of the respective envelopes of the images of the plurality of images.

The processor 8 then calculates a metric representative of a focus quality in a region of interest of the composite image IC (step 304). The region of interest chosen is typically a region showing the endosteum E and/or the cortical bone tissue (internal medium).

The metric is preferably a function of the mean intensity and/or mean contrast in the region of interest considered in the composite image IC.

The metric is typically one of or a combination of the following metrics, known in the state of the art:

The metric of the image intensity,

The metric of the lateral spectral energy described in the document "Sound speed correction in ultrasound image" by D. Napolitano, C. Chou, G. McLaughlin et al., published in 2006, the so-called "Brenner sharpness criterion" metric or the so-called "Tenenbaum sharpness criterion" metric or the so-called "normalized variance sharpness criterion" metric, all described in the document "Automatic sound speed selection in photoacoustic image reconstruction using an autofocus approach", by B. Treeby, T. Varslot, E. Zhang et al., published in 2011.

The steps 300, 302 and 304 are repeated for different pairs of candidate values for the parameters $\delta^*$ and $\beta_0$. At the end of this repetition, as many metrics as pairs of candidate values used are thus obtained.

The processor 8 then selects as definitive values for the parameters $\delta^*$ and $\beta_0$ a pair of optimal values from among the pairs of candidate values used (step 306). The processor 8 is based on the calculated metrics for this.

The pair of candidate values selected during step 306 is the one which served as the input data point to produce a composite image IC whose associated metric is indicative of a maximum focus quality in the region of interest considered among all the metrics calculated. Typically, when one of the methods listed above is used to calculate the metric, a metric of maximal value among all the metrics calculated is sought.

Ultimately, a candidate value pair that has been used is selected or not at step 306 based on the metric that has been calculated based on that pair.

The processor 8 now knows the four Thomsen parameters $\alpha_0, \beta_0, \delta_0^*, \in$, which constitute the characteristics indicative of the propagation of ultrasonic waves in the bone B.

Returning to FIG. 6, these parameters can advantageously be exploited as follows.

The processor 8 locates the endosteum E (step 210) in one of the images constructed during step 208. During the location step 210, the processor 8 generates location data of the endosteum E.

The location 210 of the endosteum E conventionally comprises the following substeps:

The image chosen for the location is segmented, so as to identify a group of pixels showing the endosteum E (this segmentation comprising, for example, the implementation of a Dijkstra's algorithm known from the state of the art).

This group of pixels is approximated into a demarcation curve defined by a polynomial, for example a parabola.

The location data of the endosteum E obtained during step 210 differ from those obtained during step 110 in that it is based on images in different planes (transverse plane for step 110 versus longitudinal plane for step 210).

Preferentially, the location 210 is implemented in one of the preliminary images constructed on the basis of candidate values having been selected as such for the parameters $\delta^*$, $\beta_0$ in step 306. This image can thus be the first image I1, the second image I2, the third image I3, the fourth image I4 or the composite image IC. This has the advantage of locating the endosteum E more precisely due to the high focus quality of these images among all those which have been constructed by the processor 8.

Very preferentially, it is the first image I1 constructed on the basis of candidate values having been selected as values for the parameters $\delta^*$, $\beta_0$ during step 306 which is used for the location of the endosteum during step 210. Indeed, it is this first image I1 that makes it possible to locate the endosteum E more precisely, this first image I1 being associated with waves having a mode which does not change when crossing the periosteum PE and which does not change when reflecting in the endosteum E.

Next, the processor 8 estimates a thickness of the bone B, measured between the periosteum PE and the endosteum E (step 212). This thickness is estimated on the basis of location data obtained in steps 106 and 210.

The thickness estimated at step 212 constitutes additional information to the thickness estimated at step 112. Indeed, the thickness estimated at step 212 is a thickness measured in a longitudinal plane of the bone B, while the thickness estimated in step 112 is a thickness measured in a transverse plane of bone B. These two thicknesses are generally different and therefore constitute mutually complementary information.

3) Second Embodiment of the Characterisation Method, Based on an Elastic Isotropy Model In a first embodiment of the method described above, the fairly realistic assumption has been made that bone is an elastically anisotropic medium, but elastically isotropic in its transverse plane.

By the present, a method will be described according to a second embodiment in which the assumption is made that the bone B is elastically isotropic. In other words, the propagation speed of sound in the bone B is the same in all directions. This model is more approximate than the one used in the first embodiment described previously but has the advantage of leading to simpler processing, which will presently be described.

Figure 10:
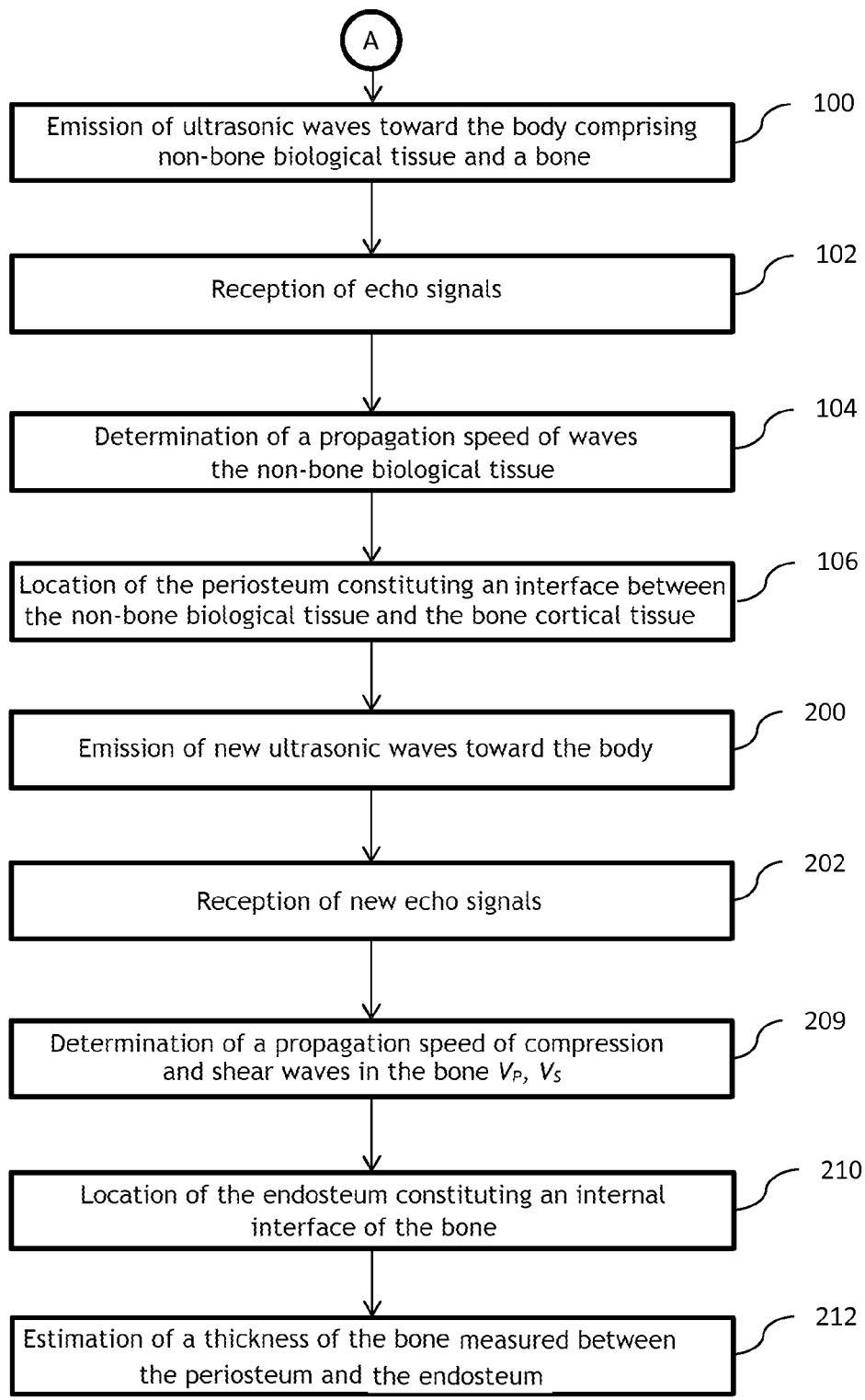
FIG. 10 is a flow chart of the steps of a characterisation method according to a second embodiment of the invention.

In reference to FIG. 10, the method according to this second embodiment comprises the steps 100, 102, 104, 106, 200, 202 described previously.

The processor 8 jointly determines two speeds on the basis of echo signals received in step 202: one compression wave propagation speed in the bone $V_P$, and one shear wave propagation speed $V_S$ in the bone (step 209).

Figure 11:
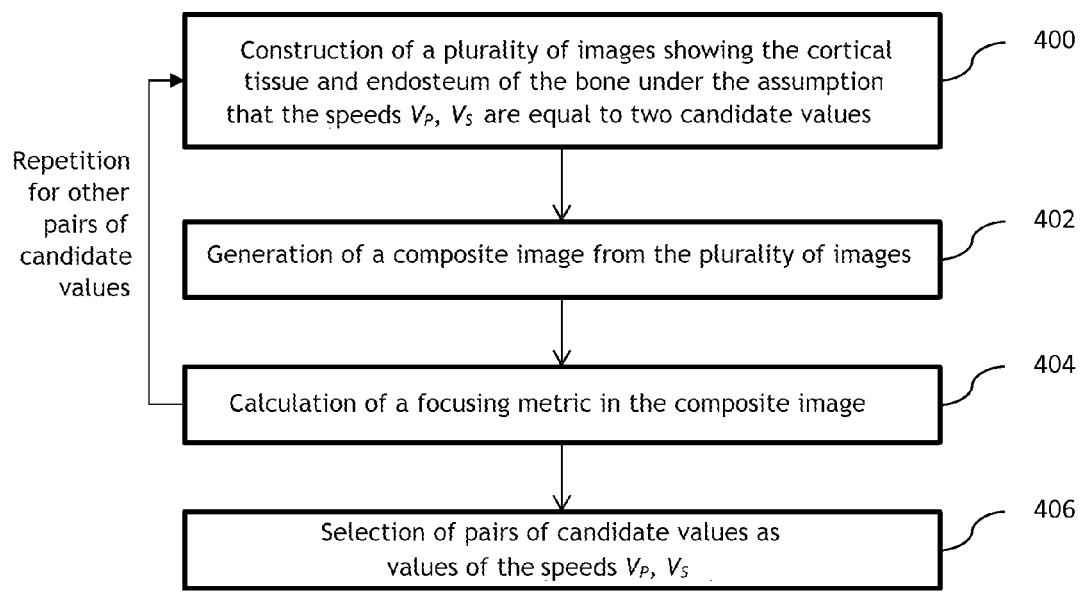
FIG. 11 is a flow chart detailing the substeps of a step illustrated in FIG. 10.

In reference to FIG. 11, step 209 comprises the following substeps.

The processor 8 constructs a plurality of images each showing the endosteum E (internal interface) and the cortical tissue of the bone (internal medium) (step 400). For this set 400, the following input data are used by the processor 8:

The echo signals acquired in step 202.

The location data of the periosteum PE (external interface) obtained in step 106.

The speed of sound in the non-bone biological tissue (external medium) determined in step 108.

Two candidate values which are available in the memory 10.

During step 400, the processor 8 implements a processing making the assumption that the speeds $V_P$ and $V_S$ are respectively equal to these two candidate values. This assumption is therefore different than the one used during step 300 forming part of the method according to the first embodiment.

Except for this different assumption, all the other principles of step 300 described previously can be repeated in step 400. The plurality of images constructed during step 400 can thus comprise:

a first image I1 selectively constructed on the basis of the first echo signals, when the first waves are part of the ultrasonic waves transmitted in step 202 and/or a second image I2 selectively constructed on the basis of the second echo signals, when the second waves are part of the ultrasonic waves transmitted in step 202 and/or a third image I3 selectively constructed on the basis of the third echo signals, when the third waves are part of the ultrasonic waves transmitted in step 202 and/or a fourth image I4 selectively constructed on the basis of the fourth echo signals, when the fourth waves are part of the ultrasonic waves transmitted in step 202.

The processor 8 then generates a composite image IC on the basis of the plurality of images (step 402). This step 402 can be identical to step 302.

The processor 8 then calculates a metric representative of a focus quality in a region of interest of the composite image IC (step 404). The region of interest chosen is typically a region showing the endosteum E and/or the cortical bone tissue (internal medium). This step 404 can be identical to step 304.

The steps 400, 402 and 404 are repeated for different pairs of candidate values for the speeds $V_P$ and $V_S$. At the end of this repetition, as many metrics as pairs of candidate values used are thus obtained.

The processor 8 then selects as definitive values for the speeds $V_P$ and $V_S$ a pair of optimal values from among the pairs of candidate values used (step 406). The processor 8 is based on the calculated metrics for this. The principles implemented in step 306 are applicable to step 406.

Ultimately, steps 208 and 209 have for a common point determining two parameters indicative of the propagation of ultrasonic waves in the bone B. In step 208 used in the first embodiment, these two parameters are $\delta^*$, $\beta_0$ Thomsen parameters. In step 209, used in the second embodiment, these two parameters are the speeds $V_P$ and $V_S$.

Steps 210, 212 are implemented as in the first embodiment. The same principles apply concerning the selection of the image used to locate the endosteum E.

4) Other Applications

Although advantageous to characterize a bone, the system 1 and the methods described above can also be applied for the characterisation of other objects, provided that the following conditions are satisfied.

The object to characterise comprises:

An external interface (the periosteum PE when this object is the bone B) that can be crossed by ultrasonic waves.

An internal medium (cortical bone tissue, when this object is the bone B) in which ultrasonic waves can propagate.

An internal interface (the endosteum E when this object is the bone B) that can reflect ultrasonic waves.

In return, the object is not necessarily tubular in shape or tubular overall, as is the case of bone B. The object can, for example, be in the form of a plate, the internal and external interfaces then defining two opposite sides of such a plate.

For example, the internal medium comprises pores containing a fluid and oriented in a same longitudinal direction or solid fibres oriented in the same longitudinal direction, for example glass or carbon fibres.

The object can, in particular, imitate a bone and be intended to be used for training purposes by medical personnel.

The invention claimed is:

1. A method comprising:

transmitting, by transmitters, ultrasonic waves toward an object comprising an external interface, an internal interface and an internal medium located between the external interface and the internal interface, so that the ultrasonic waves propagate in an external medium located between the transmitters and the object, then enter into the object by crossing the external interface, then reflect on the internal surface, then exit the object by crossing the external interface again, the ultrasonic waves comprising first waves having a mode which evolves according to a first evolution during their propagation in the object and second waves having a mode which evolves according to a second evolution during their propagation in the object, the second evolution being different from the first evolution, receiving, by receivers, echo signals having exited the object, the echo signals comprising first signals representing echoes of the first waves and second signals representing echoes of the second waves, determining two characteristics of the object indicative of a propagation of ultrasonic waves in the object, wherein determining the two characteristics of the object comprises:

a) constructing a plurality of images showing the internal interface and the internal medium, the plurality of images being constructed from the echo signals, location data of the external interface, a speed of sound in the external medium and under the assumption that the two characteristics of the object are respectively equal to two candidate values, the plurality of images comprising a first image associated with the first waves and constructed from the first signals, and a second image associated with the second waves and constructed from the second signals, b) constructing a composite image from the plurality of images, c) computing a metric indicative of a focus quality of at least one of the internal interface and of the internal medium in the composite image, d) depending on the metric, selecting or not the two candidate values as respective values of the two characteristics of the object.

2. The method according to claim 1, wherein:

the ultrasonic waves comprise third waves having a mode which evolves according to a third evolution during their propagation in the object, the third evolution being different from the first evolution and the second evolution, the echo signals comprise third signals representing echoes of the third waves, the plurality of images comprises a third image associated with the third waves and constructed from the third signals.

3. The method according to claim 2, wherein:

the ultrasonic waves comprise fourth waves having a mode which evolves according to a fourth evolution during their propagation in the object, the fourth evolution being different from the first evolution, the second evolution and the third evolution, the echo signals comprise fourth signals representing echoes of the fourth waves, the plurality of images comprises a fourth image associated with the fourth waves and constructed from the fourth signals.

4. The method according to claim 1, wherein the ultrasonic waves comprise at least of:

waves having a mode which does not change when crossing the external interface and does not change when reflecting on the internal interface, waves having a mode which changes when they enter into the object by crossing the external interface, which does not change when they are reflected on the internal interface and which changes again when they exit the object by crossing the external interface, waves having a mode which changes when they enter into the object by crossing the external interface, which changes again when they are reflected on the internal interface and which does not change when they exit the object by crossing the external interface, and waves having a mode which does not change when they enter into the object by crossing the external interface, which changes when they are reflected on the internal interface and which changes again when they exit the object by crossing the external interface.

5. Method according to claim 1, wherein the ultrasonic waves are compression waves at their emission.

6. The method according to claim 1, wherein the two characteristics of the object comprise an elastic anisotropy parameter of the object and a propagation speed of shear waves in the object which are polarised in a direction parallel or perpendicular to a longitudinal axis of the object.

7. The method according to claim 1, wherein the plurality of images is constructed under the assumption that the object is elastically isotropic in a plane perpendicular to a longitudinal axis of the object.

8. The method according to claim 1, wherein the two parameters are adapted to define, in combination with two other parameters:

a calculation function of a propagation speed of a compression wave in the object in any direction of propagation, and a calculation function of a propagation speed of a shear wave in the object which is polarized in any direction.

9. The method according to claim 8, wherein the two other parameters comprise a propagation speed of compression waves in an axial direction of the object and another parameter of elastic anisotropy of the object.

10. The method according to claim 1, wherein the two characteristics of the object comprise a propagation speed of compression waves in the object and a propagation speed of shear waves in the object.

11. The method according to claim 10, wherein the plurality of images is constructed under the assumption that the object is elastically isotropic.

12. The method according to claim 1, wherein constructing the plurality of images comprises:

estimating trajectories followed by the first waves from the first signals, from location data of the external interface, and under the assumption that the two characteristics of the object are respectively equal to the two candidate values, computing a duration of propagation of ultrasonic waves via the trajectories, computing an intensity of a pixel of the first image, from the duration of propagation, the reference signals and positions of the transmitters and of the receivers.

13. The method according to claim 1, wherein constructing the composite image comprises computing a weighted sum of the plurality of images.

14. The method according to claim 1, comprising repeating steps a) to c) for different pairs of candidate values, so as to obtain a plurality of metrics, one of the pairs of candidate values being selected at step d) on the basis of the plurality of metrics.

15. The method according to claim 1, comprising locating the internal interface in an image constructed at step a) or step b), so as to generate location data of the internal interface.

16. The method according to claim 15, wherein the internal interface is located in an image constructed from two candidate values selected at step d) as the respective values of the two characteristics of the object.

17. The method according to claim 15, wherein the internal interface is located in an image constructed from wave echo signals having a mode which does not change when crossing the external interface and which does not change when reflecting on the internal interface.

18. The method according to claim 15, comprising estimating a thickness of the object between the external interface and the internal interface, from location data of the external interface and location data of the internal interface.

19. The method according to claim 1, wherein the object is a bone, the external interface is a bone periosteum, the interface is a bone endosteum and the internal medium is a bone cortical tissue.

20. The method according to claim 1, wherein the internal medium comprises pores containing a fluid or solid fibres oriented in the same longitudinal direction.

21. A system comprising:

transmitters configured to transmit ultrasonic waves toward an object comprising an external interface, an internal interface and an internal medium located between the external interface and the internal interface, so that ultrasonic waves propagate in an external medium located between the transmitters and the object, then enter into the object by crossing the external interface, then reflect on the internal surface, then exit the object by crossing the external interface again, the ultrasonic waves comprising first waves having a mode which evolves according to a first evolution during their propagation in the object and second waves having a mode which evolves according to a second evolution during their propagation in the object, the second evolution being different from the first evolution, receivers, configured to receive echo signals having exited the object, the echo signals comprising first signals representing echoes of the first waves and second signals representing echoes of the second waves, a processing device configured to determine two characteristics of the object indicative of the propagation of ultrasonic waves in the object, wherein determining the two characteristics of the object comprises:

a) constructing a plurality of images showing the internal interface and the internal medium, the plurality of images being constructed from the echo signals, location data of the external interface, a speed of sound in the external medium and under the assumption that the two characteristics of the object are respectively equal to two candidate values, the plurality of images comprising a first image associated with the first waves and constructed from the first signals, and a second image associated with the second waves and constructed from the second signals, b) constructing a composite image from the plurality of images, c) computing a metric indicative of a focus quality of at least one of the internal interface and the internal medium in the composite image,
d) depending on the metric, selecting or not of the two candidate values as respective values of the two characteristics of the object.

* * * * *